United States Patent [19]
Shiiki et al.

[11] Patent Number: 5,830,991
[45] Date of Patent: Nov. 3, 1998

[54] PREPARATION PROCESS AND PURIFICATION PROCESS OF DIMERIC CYCLIC ESTER OF HYDROXYCARBOXYLIC ACID

[75] Inventors: Zenya Shiiki, Narashino; Yukichika Kawakami, Iwaki, both of Japan

[73] Assignee: Kureha Kagaku Kagyo KK, Tokyo, Japan

[21] Appl. No.: 788,907

[22] Filed: Jan. 23, 1997

[30]      Foreign Application Priority Data

Feb. 9, 1996  [JP]  Japan ................................. 8-048000
Apr. 10, 1996 [JP]  Japan ................................. 8-113139

[51] Int. Cl.⁶ ................................. C08F 6/00; C08J 3/00
[52] U.S. Cl. ................... 528/491; 528/481; 528/487; 528/491; 528/494; 528/495; 528/501; 528/502; 528/503; 524/706; 524/755; 524/765; 524/758; 549/274
[58] Field of Search ................... 528/481, 487, 528/491, 494, 495, 501, 502, 503; 524/706, 755, 765, 768; 549/274

[56]           References Cited

U.S. PATENT DOCUMENTS

| | | | |
|---|---|---|---|
| 2,668,162 | 2/1954 | Lowe | 528/357 |
| 4,727,163 | 2/1988 | Bellis | 549/274 |
| 4,835,293 | 5/1989 | Bhatia | 549/274 |
| 5,326,887 | 7/1994 | Di Cosimo et al. | 549/274 |
| 5,342,969 | 8/1994 | Ford et al. | 549/274 |

FOREIGN PATENT DOCUMENTS

| | | |
|---|---|---|
| 2692263 | 12/1993 | France . |
| 9215572 | 9/1992 | WIPO . |
| WO 92 15572 | 9/1992 | WIPO . |
| WO 9302075 | 2/1993 | WIPO . |
| WO 9509142 | 4/1995 | WIPO . |

*Primary Examiner*—Samuel A. Acquah
*Attorney, Agent, or Firm*—Dinsmore & Shohl LLP

[57]            ABSTRACT

The invention provides an economical and efficient process for preparing a dimeric cyclic ester of an α-hydroxycarboxylic acid by depolymerizing a corresponding α-hydroxycarboxylic acid oligomer, which comprises the steps of (1) heating a mixture containing the α-hydroxycarboxylic acid oligomer and at least one high-boiling polar organic solvent having a boiling point within a range of 230°–450° C. to a temperature, at which the depolymerization of the oligomer takes place, under atmospheric pressure or reduced pressure, (2) dissolving the oligomer in the solvent until a residual rate of a melt phase of the oligomer reaches 0.5 or lower, (3) further continuing the heating at the temperature, at which the depolymerization of the oligomer takes place, to depolymerize the oligomer, (4) distilling out the dimeric cyclic ester formed together with the high-boiling polar organic solvent, and (5) recovering the dimeric cyclic ester from the distillate. The invention also provides a process for purifying a crude dimeric cyclic ester of an α-hydroxycarboxylic acid.

21 Claims, No Drawings

PREPARATION PROCESS AND PURIFICATION PROCESS OF DIMERIC CYCLIC ESTER OF HYDROXYCARBOXYLIC ACID

FIELD OF THE INVENTION

The present invention relates to a process for preparing a dimeric cyclic ester of an α-hydroxycarboxylic acid, and more particularly to a process for economically and efficiently preparing a dimeric cyclic ester by heating an α-hydroxycarboxylic acid oligomer in a state of solution to depolymerize it. This invention also relates to a process for purifying a dimeric cyclic ester of an α-hydroxycarboxylic acid. The dimeric cyclic ester obtained by the process of the present invention can be used as a starting material (monomer) for a poly(α-hydroxycarboxylic ester) useful as a biodegradable polymer, medical polymer or the like.

BACKGROUND OF THE INVENTION

It is a known technique to depolymerize an oligomer of an α-hydroxycarboxylic acid (hereinafter may be abbreviated as "α-HCA"), thereby preparing a dimeric cyclic ester (hereinafter may be abbreviated as "DCE") of the α-hydroxycarboxylic acid. Here, the dimeric cyclic ester of the α-hydroxycarboxylic acid means a compound having a structure that a dimer of the α-hydroxycarboxylic acid is cyclized in the form of an ester. For example, glycolide is typical of the dimeric cyclic ester of the α-hydroxycarboxylic acid and has a structure that two molecules of glycolic acid (i.e., hydroxyacetic acid) are bonded in the form of an anhydride to form a cyclic ester (i.e., diglycolic anhydride).

In the past, the following various processes have been proposed to obtain, for example, glycolide.

(i) U.S. Pat. No. 2,668,162 discloses a process in which a glycolic acid oligomer is ground to powder and heated (at 270°–285° C.) under an ultra-high vacuum (12–15 Torr) while feeding to a reaction vessel by extreme bits (about 20 g/hr) to depolymerize it, and the product is collected in a trap. Although this process is feasible on a small scale, it is difficult to enlarge the scale. Therefore, the process is unfit for mass production. In addition, according to this process, the oligomer remains in the reaction vessel as an excessive residue in the form of tar upon the heating, and so the process suffers from low yield and troublesome removal of the residue. Further, since the resultant dimeric cyclic ester is a crystal having a high melting point, there is a possibility that it may accumulate on the inner wall surface of a recovery line to block the line. It is also difficult to recover the accumulated product in the line.

(ii) U.S. Pat. No. 4,727,163 discloses a process in which a great amount of a polyether is used as a substrate, a block copolymer of the polyether with a small amount of glycolic acid is formed, and the copolymer is then heated and depolymerized to obtain a dimeric cyclic ester. However, the block copolymerization process suffers from a complicated operation and too high cost. In addition, according to this process, a great amount of tar remains as a residue, and so the process also suffers from low yield and troublesome cleaning inside a reaction vessel. Further, there is a possibility that the dimeric cyclic ester formed may accumulate on the inner wall surface of a recovery line to block the line. Therefore, this process is unfit for mass production by scale-up.

(iii) U.S. Pat. No. 4,835,293 discloses a process in which a glycolic acid oligomer is heated into a melt, a nitrogen gas is blown into the surface of the melt so as to widen the surface area of the melt to some extent, and a dimeric cyclic ester generated and vaporized from the surface of the melt is carried with the gas stream to collect it. According to this process, in order to generate and vaporize the dimeric cyclic ester from the surface of the melt of the oligomer as quickly as possible, a stream of nitrogen gas is blown into the melt to widen the surface area of the melt. However, the surface area is yet extremely small, and so the rate of formation of the dimeric cyclic ester is low. In addition, tar formation progresses in the interior of the oligomer melt during the heating, and excessive tar remains as a residue in a reaction vessel. Therefore, this process suffers from low yield and troublesome cleaning inside the reaction vessel.

(iv) U.S. Pat. No. 5,326,887 and WO92/15572A1 disclose a process in which a glycolic acid oligomer is heated and depolymerized over a fixed bed catalist to obtain a dimeric cyclic ester. According to this process, a considerable amount of tar is formed upon the heating and remains as a residue. Therefore, the process suffers from low yield and troublesome cleaning on the fixed bed.

According to the conventional processes, as described above, a dimeric cyclic ester of an α-hydroxy-carboxylic acid has not been able to be mass-produced economically and efficiently. The reason for it is that the conventional processes for preparing a dimeric cyclic ester by the depolymerization of an α-hydroxycarboxylic acid oligomer are, in principle, processes in which the oligomer in a solid state is heated into a melt, and the dimeric cyclic ester, which is a depolymerized product, is vaporized out of the surface of this melt phase to collect it, and hence involve the following problems.

(1) Since the surface area of the melt phase of the oligomer is small, the generation rate or vaporization rate of the dimeric cyclic ester is low.

(2) Since polycondensation progresses in the interior of the melt phase of the oligomer due to the long-time heating, and tar is formed in a great amount, the yield of the dimeric cyclic ester is reduced, and moreover the tar residue makes cleaning troublesome.

(3) Since the dimeric cyclic ester vaporized is a crystal having a high melting point, it tends to accumulate on the inner wall surface of a distillation line and has a possibility that the line may be blocked. It is also difficult to recover the dimeric cyclic ester accumulated on the inner wall surface of the line.

For the above-described reasons, the processes of heating the α-hydroxycarboxylic acid oligomer as it is to depolymerize it have been extremely difficult to mass-produce the dimeric cyclic ester by scale-up.

OBJECTS AND SUMMARY OF THE INVENTION

It is an object of the present invention to provide a process for economically and efficiently preparing a dimeric cyclic ester from an α-hydroxycarboxylic acid oligomer.

Another object of the present invention is to provide a process for economically and efficiently purifying a crude dimeric cyclic ester of an α-hydroxycarboxylic acid.

The present inventors have carried out an extensive investigation with a view toward overcoming the above -described problems involved in the prior art. As a result, it has been found that a dimeric cyclic ester can be economically and efficiently provided by mixing an α-hydroxycarboxylic acid oligomer with a high-boiling polar organic solvent, heating the mixture to dissolve the oligomer in the solvent in a state of solution phase, preferably, substantially uniform solution phase, further heating the solution in this state to depolymerize the oligomer and distilling out the dimeric cyclic ester formed together with the solvent. According to this process, the dimeric cyclic ester can be mass-produced. It has also been found that a purified dimeric cyclic ester can be economically and efficiently provided by mixing a crude dimeric cyclic ester of an α-hydroxycarboxylic acid obtained by any one of various processes such as the above-described conventional processes with a high-boiling polar organic solvent and heating the mixture in a state of uniform solution phase to distill out the dimeric cyclic ester together with the solvent.

The present invention has been led to completion on the basis of these findings.

According to the present invention, there is thus provided a process for preparing a dimeric cyclic ester of an α-hydroxycarboxylic acid by depolymerizing a corresponding α-hydroxycarboxylic acid oligomer, which comprises the steps of:

(1) heating a mixture containing the α-hydroxy-carboxylic acid oligomer and at least one high-boiling polar organic solvent having a boiling point within a range of 230°–450° C. to a temperature, at which the depolymerization of the oligomer takes place, under atmospheric pressure or reduced pressure;

(2) dissolving the oligomer in the solvent until a residual rate of a melt phase of the oligomer reaches 0.5 or lower;

(3) further continuing the heating at the temperature, at which the depolymerization of the oligomer takes place, to depolymerize the oligomer;

(4) distilling out the dimeric cyclic ester formed together with the high-boiling polar organic solvent; and (5) recovering the dimeric cyclic ester from the distillate.

The term "residual rate of the melt phase" as used herein means a ratio of the volume of a melt phase of the α-hydroxycarboxylic acid oligomer formed in a solvent actually used to the volume of a melt phase of the oligomer formed in a solvent substantially having no dissolving power for the oligomer, such as liquid paraffin, where the latter volume is regarded as 1. A lower residual rate of the melt phase indicates that the solvent has greater dissolving power for the oligomer.

According to the present invention, there is also provided a process for purifying a crude dimeric cyclic ester of an α-hydroxycarboxylic acid, which comprises the steps of:

heating a mixture containing the crude dimeric cyclic ester of the α-hydroxycarboxylic acid and at least one high-boiling polar organic solvent having a boiling point within a range of 230°–450° C. to a temperature of at least 230° C. under atmospheric pressure or reduced pressure to form a uniform solution free from phase separation between the individual components;

further continuing the heating in the state of uniform solution phase to distill out the dimeric cyclic ester together with the high-boiling polar organic solvent; and recovering the dimeric cyclic ester from the distillate.

DETAILED DESCRIPTION OF PREFERRED EMBODIMENTS

The preparation process of a dimeric cyclic ester of an α-hydroxycarboxylic acid according to the present invention is a process to be called, so to say, "solution-phase depolymerization process". According to this preparation process, the dimeric cyclic ester can be efficiently produced, which is considered to be due to the following reasons.

(1) Since the depolymerization of the α-hydroxy-carboxylic acid oligomer is caused in its solution phase, preferably, its uniform solution phase, whereby the surface area of the oligomer existing in the solution phase is widened to an extremely great extent, the rate of formation of the dimeric cyclic ester generated and vaporized from the surface of the oligomer is accelerated by leaps and bounds.

(2) Since contact between oligomer molecules is limited by the solvent, the polycondensation reaction of the oligomer upon the heating is prevented from progressing, and so the amount of tar formed is extremely reduced. Therefore, it is possible to enhance the yield of the dimeric cyclic ester and to almost save one the trouble of cleaning the interior of a reaction vessel.

(3) Since the dimeric cyclic ester is formed at a distilling temperature of the high-boiling polar organic solvent and distilled out together with the solvent, it scarcely accumulates on the inner wall surface of a recovery line. Therefore, the blockage of the line is prevented, and one can be saved the trouble of recovering the product accumulated on the interior of the line.

(4) Above all, since a system similar to an ordinary distillation system for solvents may be used, a scale can be enlarged with ease, and so mass production on an industrial scale is also easily performed.

α-Hydroxycarboxylic acid

The preparation process of the present invention can be applied to production processes of dimeric cyclic esters of α-hydroxycarboxylic acids such as glycolic acid, lactic acid, α-hydroxybutyric acid and α-hydroxyvaleric acid. Various dimeric cyclic esters such as glycolide and lactide can be prepared by depolymerizing oligomers of these α-hydroxycarboxylic acids in a solution phase according to the process of the present invention. The process of the present invention is particularly suitable for use in the preparation of glycolide.

High-boiling polar organic solvent

The solvent used in the depolymerization of the α-hydroxycarboxylic acid oligomer in the preparation process of the present invention is a high-boiling organic solvent having a boiling point within a range of 230°–450° C., preferably 235°–450° C., more preferably 260°–430° C., most preferably 280°–420° C. If the boiling point of the solvent is lower than 230° C., it is difficult to depolymerize (in particular, under reduced pressure) the α-hydroxy-carboxylic acid oligomer. The depolymerization of the oligomer generally requires heating the oligomer to a temperature of at least 230° C. Further, if the boiling point of the solvent is lower than 230° C., only the solvent having a lower boiling point is distilled out earlier than the dimeric cyclic ester even if the dimeric cyclic ester is formed by the depolymerization, and so it is difficult to distill out the dimeric cyclic ester together with the solvent. On the other hand, if the boiling point of the solvent exceeds 450° C., the solvent is hard to be distilled out, and so it is difficult to co-distill out the solvent with the distilling-out of the dimeric cyclic ester formed by the depolymerization.

The high-boiling polar organic solvent generally has a molecular weight within a range of 150–500, preferably 180–450, more preferably 200–400. It is not preferable to use any organic solvent having a molecular weight outside the range of 150–500 because it is difficult to distill out the solvent together with the dimeric cyclic ester.

The solvent used in the depolymerization in the preparation process of the present invention is a polar organic solvent. Nonpolar or semipolar organic solvents are hard to form a uniform solution phase with the oligomer and easy to undergo phase separation. Such nonpolar or semipolar organic solvents are also easy to undergo phase separation even when they are used in combination with a solubilizing agent which will be described subsequently. Further, when the depolymerization is performed with a nonpolar or semipolar organic solvent, the dimeric cyclic ester formed tends to accumulate on the inner wall surface of a recovery line and hence to cause the blockage of the line even when the solvent is distilled out together with the dimeric cyclic ester formed by the depolymerization.

The solvent used in the depolymerization in the preparation process of the present invention is desirably not basic. Basic organic solvent, for example, amine type solvents, pyridine type solvents, quinoline type solvents, etc., have a possibility that they may react with the α-hydroxycarboxylic acid oligomer used and the dimeric cyclic ester formed. It is hence not preferable to use such a basic organic solvent.

Examples of such high-boiling polar organic solvents having high dissolving power for the α-hydroxycarboxylic acid oligomer include alkoxyalkyl esters of aromatic carboxylic acids, alkoxyalkyl esters of aliphatic carboxylic acids, polyalkylene glycol ethers and polyalkylene glycol esters. When these high-boiling polar organic solvents are used by themselves in a proportion of generally 0.3–50 times by weight to the α-hydroxycarboxylic acid oligomer, they have dissolving power capable of dissolving the α-hydroxycarboxylic acid oligomer within the above-described concentration range at a temperature (at least 230° C.) at which the depolymerization of the oligomer takes place. Of these, bis(alkoxyalkyl) phthalates such as di(2-methoxyethyl) phthalate, dialkylene glycol dibenzoates such as diethylene glycol dibenzoate, and polyethylene glycol ethers such as hexaethylene glycol dimethyl ether are particularly preferred from the viewpoints of dissolving power for the oligomers, chemical stability and thermal stability. These high-boiling polar organic solvents having high dissolving power are referred to as the solvents of Group (a).

In the present invention, high-boiling polar organic solvents having lower dissolving power for the oligomers than those of Group (a) may be used. Examples thereof include aromatic carboxylic esters, aliphatic carboxylic esters, aromatic ethers, aliphatic ethers, aromatic phosphoric esters, aliphatic phosphoric esters, aliphatic imide compounds, aliphatic amide compounds and polyhalogenated aromatic hydrocarbons. These high-boiling polar organic solvents are lower than the solvents of Group (a) in the dissolving power that they can dissolve the α-hydroxycarboxylic acid oligomer by themselves at a temperature at which the depolymerization of the oligomer takes place. These high-boiling polar organic solvents having lower dissolving power are referred to as the solvents of Group (b). These solvents of Group (b) are generally used in combination with a solvent of Group (a) or with a solubilizing agent.

Of the solvents of Group (b), the aromatic carboxylic esters, aliphatic carboxylic esters and aromatic phosphoric esters are particularly preferred from the viewpoints of power to dissolve out the dimeric cyclic ester, chemical stability and thermal stability. Preferable examples of the aromatic carboxylic esters include phthalic esters such as benzylbutyl phthalate, dibutyl phthalate, diamyl phthalate and dipropyl phthalate; and benzoic esters such as benzyl benzoate. Examples of the aliphatic carboxylic esters include adipic esters such as octyl adipate and sebacic esters such as dibutyl sebacate. Examples of the aromatic phosphoric esters include tricresyl phosphate.

Many of the solvents of Group (b) can only partially dissolve the α-hydroxycarboxylic acid oligomer at a temperature, at which the depolymerization of the oligomer takes place, when the concentration of the oligomer is high. On the other hand, many of the solvents of Group (b) are cheap and moreover can provide the dimeric cyclic ester at relatively high yields when their dissolving power for the oligomer is enhanced. Therefore, the solvents of Group (b) are usually used with the solubility of the α-hydroxycarboxylic acid oligomer in such solvents enhanced by a solubilizing agent.

As a method for enhancing the dissolving power of the solvent of Group (b), there is a method in which it is mixed with the above-described solvent of Group (a) before its use. The mixing ratio (a):(b) between both solvents is generally 99:1 to 1:99 by weight.

Solubilizing agent

As a method for enhancing the solubility of the α-hydroxycarboxylic acid oligomer in the high-boiling polar organic solvent, particularly, the solvent of Group (b), there is a method making use of a solubilizing agent.

The solubilizing agent used in the present invention satisfies the following requirements:

(1) being a non-basic compound;
(2) being compatible with or soluble in the solvent used (may be either liquid or solid);
(3) having a boiling point of at least 230° C., preferably at least 250° C., with that having a boiling point higher than the solvent used being preferred because of easy handling; and
(4) having a hydrophilic functional group such as, for example, an OH, COOH or CONH group.

Among those satisfying the above requirements, solubilizing agents having an OH group are most preferred from the viewpoints of solubilizing power and stability. Accordingly, it is preferable to use that having higher hydrophilicity than the high-boiling polar organic solvent as the solubilizing agent.

Specific examples of the solubilizing agent include monohydric and dihydric or still higher polyhydric alcohols (including partial esters and ethers thereof), phenols, aliphatic monocarboxylic and di- or still higher polycarboxylic acids, aliphatic amides formed from an aliphatic carboxylic acid and an amine, aliphatic imides, and sulfones. The alcohols are particularly effective as the solubilizing agents. Among the alcohols, polypropylene glycol, polyethylene glycol, glycerol and tridecanol are preferred.

Although the action of the solubilizing agent is not yet completely clarified, it is considered to be attributable to an effect that it acts on an α-hydroxy-carboxylic acid oligomer chain at a terminal thereof to change the oligomer to soluble matter, an effect that it acts on the α-hydroxycarboxylic acid oligomer chain at an intermediate site thereof to cleave the oligomer, thereby modifying the molecular weight of the oligomer to make it soluble, an effect that the polarity of the whole solvent system is varied to enhance hydrophilicity, thereby enhancing the solubility of the oligomer in the solvent, or the combined effect thereof.

In any event, the use of this solubilizing agent permits the use of a cheap solvent of Group (b), and so it has an extremely great economical effect.

The solubilizing agent is generally used in a proportion of 0.1–500 parts by weight, preferably 1–50 parts by weight, more preferably 2–20 parts by weight per 100 parts by weight of the α-hydroxycarboxylic acid oligomer. If the proportion of the solubilizing agent is too low, its solubilizing effect is insufficient, so that phase separation is caused between the oligomer and the solvent. If the proportion of the solubilizing agent is too high, unfavorable reactions such as its reaction with the oligomer may be caused according to the kind of the solubilizing agent used, and recovery of the solubilizing agent is troublesome. It is also disadvantageous from an economical point of view.

Catalyst

In the preparation process of a dimeric cyclic ester of an α-hydroxycarboxylic acid according to the present invention, the α-hydroxycarboxylic acid oligomer is dissolved in the high-boiling polar organic solvent, whereby the surface area thereof is extremely widened. Therefore, the generation rate or vaporization rate of the dimeric cyclic ester by the depolymerization is high. A great feature of the present invention is thus to usually have no need to use any catalyst for the depolymerization. In the preparation process of the present invention, the conventional depolymerization catalysts such as tin compounds and antimony compounds rather tend to break the uniform solution phase, thereby causing phase separation, and are generally detrimental. However, it is permissible to use these catalysts so far as no detrimental influence is thereby imposed on this "solution-phase depolymerization process".

Preparation process of oligomer

The α-hydroxycarboxylic acid oligomer used as a starting material for the preparation process of the present invention can be easily synthesized in accordance with a method known per se in the art. More specifically, its corresponding α-hydroxycarboxylic acid or an ester thereof is heated at a temperature of 100°–250° C., preferably 140°–230° C. under reduced pressure, atmospheric pressure or sufficient pressure in the presence of an optional condensation catalyst or transesterification catalyst to conduct a condensation reaction or transesterification until low-molecular weight compounds such as water and alcohol substantially come not to be distilled out. After completion of the condensation reaction or transesterification, an oligomer formed may be used as a starting material for the preparation process of the present invention as it is. The oligomer thus obtained may also be taken out of the reaction system and washed with a non-solvent such as benzene or toluene to remove an unreacted compound and compounds of a low polymerization degree before its use.

The oligomer desirably has a melting point Tm of generally at least 140° C., preferably at least 160° C., more preferably at least 180° C. from the viewpoint of yield of the dimeric cyclic ester formed by the depolymerization. The melting point Tm as referred to herein is a melting point detected at the time the oligomer is heated at a rate of 10° C./min in an inert atmosphere by means of a differential scanning calorimeter (DSC).

Preparation process of dimeric cyclic ester

The preparation process of the present invention is performed in accordance with the following processes:

(1) heating a mixture containing the α-hydroxy-carboxylic acid oligomer and at least one high-boiling polar organic solvent having a boiling point within a range of 230°–450° C. to a temperature, at which the depolymerization of the oligomer takes place, under atmospheric pressure or reduced pressure;

(2) dissolving the oligomer in the solvent until a residual rate of a melt phase of the oligomer reaches 0.5 or lower;

(3) further continuing the heating at the temperature, at which the depolymerization of the oligomer takes place, to depolymerize the oligomer;

(4) distilling out a dimeric cyclic ester formed together with the high-boiling polar organic solvent; and (5) recovering the dimeric cyclic ester from the distillate.

The high-boiling polar organic solvent is used in a proportion of generally 0.3–50 times by weight, preferably 0.5–20 times by weight, more preferably 1–10 times by weight to the α-hydroxycarboxylic acid oligomer. When the high-boiling polar organic solvent is a solvent of the above-described Group (a), it may be used by itself because it has high dissolving power for the oligomer. When a solvent of the above-described Group (b) is used, it is generally used in combination with the solvent of Group (a) or with a solubilizing agent added thereto in order to enhance the solubility of the oligomer in such a solvent.

The mixture containing the α-hydroxycarboxylic acid oligomer and the high-boiling polar organic solvent, and optionally the solubilizing agent is then heated to a temperature of at least 230° C. under atmospheric pressure or reduced pressure, whereby all or most of the oligomer is dissolved in the solvent to form a solution phase. The greatest feature of the preparation process according to the present invention is that the depolymerization of the oligomer is performed in a state of solution phase. When most of the oligomer does not dissolve in the solvent at a temperature of at least 230° C., at which the depolymerization takes place, to form a melt phase, it is difficult to distill out the dimeric cyclic ester, resulting in a tendency to easily form tar in the melt phase. Most of the oligomer is continuously heated in the state of solution phase, whereby the rate of formation of the dimeric cyclic ester generated and vaporized from the surface of the oligomer is accelerated by leaps and bounds.

The heating is carried out under atmospheric pressure or reduced pressure. It is however preferable to conduct the heating under reduced pressure of 0.1–90.0 kPa (1–900 mbar). The heating is preferably performed in an inert atmosphere. The heating temperature is at least 230° C. and generally ranges from 230° from 320° C., preferably from 235° to 300° C., more preferably from 240° to 290° C. The oligomer is depolymerized by the heating, so that the dimeric cyclic ester is distilled out together with the solvent. In the present invention, at least one high-boiling polar organic solvent having a boiling point within a range of 230°–450° C. is used, thereby distilling out the dimeric cyclic ester formed together with the solvent. If the solvent is not distilled out together with the dimeric cyclic ester when distilling out the dimeric cyclic ester, the dimeric cyclic ester attaches to the inner wall surface of a line and accumulates thereon.

The dimeric cyclic ester contained in the distillate can be separated and recovered with ease by cooling the distillate and adding a non-solvent for the dimeric cyclic ester as needed, thereby solidifying and depositing the dimeric cyclic ester. The dimeric cyclic ester deposited can be further purified by separating it from the mother liquor by filtration, centrifugal precipitation, decantation or the like in accordance with a method known per se in the art and optionally washing or extracting the ester thus separated with a non-solvent such as cyclohexane or ether, or recrystallizing it from ethyl acetate or the like. Alternatively, it can also be purified by a distillation process which will be described subsequently. On the other hand, the mother liquor from which the dimeric cyclic ester has been separated may be recycled for use in a non-purified form as it is, or treated with active carbon, filtered to purify and then recycled for use, or redistilled and recycled for use.

According to the preparation process of the present invention, tar of the oligomer is scarcely formed upon the heating, and so one can be saved the trouble of cleaning the interior of a reaction vessel. If the tar attaches to the interior of the vessel due to some troubles, the vessel can be easily cleaned by placing a solvent or a solvent and the above-described solubilizing agent in the vessel and heating it. The above-described high-boiling polar organic solvents of both Groups (a) and (b) can dissolve out the dimeric cyclic ester at a temperature at which the dimeric cyclic ester is distilled out. Therefore, the dimeric cyclic ester accumulated on the inner wall surface of the distillation line is dissolved out by such a solvent, so that the blockage of the line can be prevented, and the dimeric cyclic ester is easy to be recovered.

When the mother liquor from which the dimeric cyclic ester has been separated contains, in addition to a kind of solvent, a solvent of another kind and/or a solubilizing agent, the separated mother liquor may be recycled for use in a non-purified form as it is, or treated with active carbon, filtered to purify and then recycled for use, or subjected to simple distillation or fractional distillation to recycle for use as the solvents and/or the solubilizing agent. Since the solubilizing agent is effective for dissolving the tar residue, the amount of the tar is particularly reduced when the depolymerization is carried out using the solubilizing agent, so that the cleaning of the interior of the vessel can be omitted or reduced.

Purification process

The "solution-phase depolymerization process" according to the present invention can also be applied to a purification process of a crude dimeric cyclic ester. More specifically, the crude dimeric cyclic ester can be purified in the following manner. A high-boiling polar organic solvent having dissolving power capable of dissolving a crude dimeric cyclic ester to be purified at its distillation temperature of at least 230° C. is used and added to the crude dimeric cyclic ester. The mixture is then heated to a temperature of at least 230° C. to form a uniform solution of the dimeric cyclic ester. The heating is continued in this state to distill out the dimeric cyclic ester together with the solvent. In this case, the dimeric cyclic ester is distilled out together with the solvent without undergoing ring opening polymerization. This ester-containing distillate is cooled, and added with a non-solvent for the dimeric cyclic ester as needed, thereby solidifying and depositing the dimeric cyclic ester to separate and recover the dimeric cyclic ester from the distillate.

In this purification process, not only the solvents of Group (a) but also a part of the solvents of Group (b) may be used as a solvent for the dimeric cyclic ester by themselves. The purification process of the dimeric cyclic ester according to the present invention is sharply distinguished from the purification method according to the prior art processes such as the sublimation process in that a scale can be easily enlarged, and a large amount of the dimeric cyclic ester can be purified on an industrial scale.

ADVANTAGES OF THE INVENTION

The present invention permits economical mass production of dimeric cyclic esters of α-hydroxycarboxylic acids, particularly, glycolide, which have been difficult to be mass-produced by depolymerization and hence extremely expensive. As a result, the dimeric cyclic esters of the α-hydroxycarboxylic acids, which have heretofore been applicable only to extremely special fields such as a medical field for reasons of cost, have come to be widely usable even in general purpose of plastics including biodegradable plastics which can lighten the burden imposed on the environment.

EMBODIMENTS OF THE INVENTION

The present invention will hereinafter be described more specifically by the following Synthesis Example, Examples and Comparative Examples.

SYNTHESIS EXAMPLE 1

A 5-liter autoclave was charged with 2,500 g (27.8 mol) of glycolic acid (product of Wako Pure Chemical Industries, Ltd.). While stirring under atmospheric pressure, the temperature of the contents was raised from 170° C. to 200° C. over 2 hours to heat them, whereby glycolic acid was subjected to condensation reaction while distilling out water formed. The pressures inside the autoclave was then reduced to 5.0 kPa, and the reaction product was heated at 200° C. for 2 hours, thereby distilling off low-boiling matter such as an unreacted raw material to prepare a glycolic acid oligomer.

The melting point Tm of the thus-obtained oligomer was 206° C., and its ΔHmc was 105 J/g. Incidentally, Tm is a value detected at the time the oligomer is heated at a rate of 10° C./min in an inert atmosphere by means of a DSC, and the ΔHmc is a melt enthalpy detected at this time.

EXAMPLE 1

A 300-ml flask, to which a receiver cooled with chilled water was connected, was charged with 40 g of the glycolic acid oligomer prepared in Synthesis Example 1, and 170 g of di(2-methoxyethyl) phthalate (boiling point: about 320° C.; molecular weight: 282) were added as a high-boiling polar organic solvent. The mixture of the oligomer and solvent was heated to 265°–275° C. under reduced pressure of 12.5 kPa in a nitrogen gas atmosphere. It was visually confirmed that the oligomer dissolved uniformly in the solvent without undergoing phase separation. By the heating, a depolymerization reaction was initiated, and a dimeric cyclic ester formed started being distilled out together with the solvent and collected into the receiver. The mixture was heated to continuously distill out the dimeric cyclic ester together with the solvent until the dimeric cyclic ester was substantially not distilled out, thereby collecting a distillate in the receiver.

After completion of the distilling-out, the interior of the flask was observed. As a result, a tar residue was scarcely observed. The dimeric cyclic ester was observed attaching to a distillation line between the flask and the receiver. However, an amount of the dimeric cyclic ester accumulated was slight. Cyclohexane about twice as much as the distillate by volume was added as a non-solvent to the distillate collected in the receiver. The resultant mixture was left at rest overnight to deposit a crystal of the dimeric cyclic ester, and this crystal was collected by filtration. After the dimeric cyclic ester thus obtained was washed with cyclohexane, it was recrystallized from ethyl acetate and dried under reduced pressure. The yield of the dimeric cyclic ester was 80 wt. %. Depolymerization conditions and the interior state of the flask are shown collectively in Table 1.

Incidentally, the distilling-out by the depolymerization was stopped at the time the mixture substantially ceased to distill out the dimeric cyclic ester because if the distilling-out was continued further, only the solvent was distilled out. Therefore, the yield was calculated in accordance with the following equation:

$$\text{Yield} = (a/b) \times 100$$

wherein a is an amount of the dimeric cyclic ester collected, and b is an amount of the oligomer charged.

EXAMPLE 2

A dimeric cyclic ester was prepared from the glycolic acid oligomer in the same manner as in Example 1 except that in Example 1, the high-boiling polar organic solvent and the pressure inside the flask were changed to diethylene glycol dibenzoate (boiling point: about 375° C.; molecular weight: 375) and 4.5 kPa, respectively. Depolymerization conditions, the interior state of the flask, and a yield are shown collectively in Table 1.

EXAMPLE 3

A 300-ml flask, to which a receiver cooled with chilled water was connected, was charged with 40 g of the glycolic acid oligomer prepared in Synthesis Example 1, and 170 g of benzylbutyl phthalate (boiling point: 370° C.; molecular weight: 312) as a high-boiling polar organic solvent and 4 g of polypropylene glycol (PPG#400, product of Junsei Chemical Co., Ltd.; boiling point: at least about 450° C.; molecular weight: about 400) as a solubilizing agent were added. The mixture of the oligomer, solvent and solubilizing agent was heated to 265°–275° C. under reduced pressure of 5.0 kPa in a nitrogen gas atmosphere. The oligomer dissolved uniformly in the solvent containing the solubilizing agent to start depolymerizing. When the heating was continued at a temperature within the above range, a dimeric cyclic ester formed was distilled out together with the solvent and collected into the receiver. The dimeric cyclic ester was continuously distilled out together with the solvent until the mixture substantially ceased to distill out the dimeric cyclic ester, thereby collecting a distillate in the receiver.

After completion of the distilling-out, the interior of the flask was observed. As a result, a tar residue was scarcely observed. The dimeric cyclic ester was observed attaching to a distillation line between the flask and the receiver. However, an amount of the cyclic ester accumulated was slight. Cyclohexane about twice as much as the distillate by volume was added as a non-solvent to the distillate collected in the receiver. The resultant mixture was left at rest overnight to deposit a crystal of the dimeric cyclic ester, and this crystal was collected by filtration. After the dimeric cyclic ester thus obtained was washed with cyclohexane, it was recrystallized from ethyl acetate and dried under reduced pressure. The yield of the dimeric cyclic ester was 85 wt. %. Depolymerization conditions, the interior state of the flask and the yield are shown collectively in Table 1.

EXAMPLE 4

A dimeric cyclic ester was prepared from the glycolic acid oligomer in the same manner as in Example 3 except that in Example 3, the high-boiling polar organic solvent, the solubilizing agent and the pressure inside the flask were changed to dibutyl phthalate (boiling point: about 340° C.; molecular weight: 278), 8 g of polypropylene glycol (PPG#400, product of Junsei Chemical Co., Ltd.; boiling point: at least about 450° C.; molecular weight: about 400) and 20.0 kPa, respectively. Depolymerization conditions, the interior state of the flask, and a yield are shown collectively in Table 1.

EXAMPLE 5

A dimeric cyclic ester was prepared from the glycolic acid oligomer in the same manner as in Example 3 except that in Example 3, the high-boiling polar organic solvent, the solubilizing agent and the pressure inside the flask were changed to tricresyl phosphate (boiling point: about 420° C.; molecular weight: 368), 8.4 g of polypropylene glycol (PPG#400, product of Junsei Chemical Co., Ltd.; boiling point: at least about 450° C.; molecular weight: about 400) and 0.7 kPa, respectively. Depolymerization conditions, the interior state of the flask, and a yield are shown collectively in Table 1.

EXAMPLE 6

A dimeric cyclic ester was prepared from the glycolic acid oligomer in the same manner as in Example 3 except that in Example 3, the solubilizing agent was changed to 2.4 g of polyethylene glycol (PEG#300, product of Junsei Chemical Co., Ltd.; boiling point: at least about 400° C.; molecular weight: about 300). Depolymerization conditions, the interior state of the flask, and a yield are shown collectively in Table 1.

EXAMPLE 7

A dimeric cyclic ester was prepared from the glycolic acid oligomer in the same manner as in Example 3 except that in Example 3, the high-boiling polar organic solvent, the solubilizing agent and the pressure inside the flask were changed to benzylbutyl phthalate (boiling point: 370° C.; molecular weight: 312), 3.2 g of glycerol (product of Junsei Chemical Co., Ltd.; boiling point: at least about 290° C.; molecular weight: 92) and 5.0 kPa, respectively. Depolymerization conditions, the interior state of the flask, and a yield are shown collectively in Table 1.

EXAMPLE 8

A dimeric cyclic ester was prepared from the glycolic acid oligomer in the same manner as in Example 3 except that in Example 3, the solubilizing agent was changed to 2 g of tetraethylene glycol (boiling point: 327° C.; molecular weight: 194). Depolymerization conditions, the interior state of the flask, and a yield are shown collectively in Table 1.

EXAMPLE 9

A dimeric cyclic ester was prepared from the glycolic acid oligomer in the same manner as in Example 3 except that in Example 3, the solubilizing agent was changed to 10 g of tridecanol (boiling point: 274° C.; molecular weight: 200). Depolymerization conditions, the interior state of the flask, and a yield are shown collectively in Table 1.

EXAMPLE 10

A dimeric cyclic ester was prepared from the glycolic acid oligomer in the same manner as in Example 3 except that in Example 3, the charged amount of polypropylene glycol (PPG#400, product of Junsei Chemical Co., Ltd.; boiling point: at least about 450° C.; molecular weight: about 400) as the solubilizing agent was changed to 2.2 g. Depolymerization conditions, the interior state of the flask, and a yield are shown collectively in Table 1.

TABLE 1

| | Depolymerization conditions | | | | | | Interior State of flask | | | Residual | |
|---|---|---|---|---|---|---|---|---|---|---|---|
| | Solvent | | Solubilizing agent | | Inside temp. | Inside pressure | Melt | Accumulation of DCE on | | Yield of | rate of melt phase |
| | Kind (*1) | BP (°C.) | Kind (*2) | Amount added (parts) (*3) | of flask (°C.) | of flask (kPa) | phase of oligomer | inner wall of line | Tar formation | DCE (wt. %) | (v/v) (*4) |
| Ex. 1 | DMEP | 320 | — | — | 265–275 | 12.5 | Scarcely formed | Scarcely accumulated | Scarcely formed | 81 | 0 |
| Ex. 2 | DEDB | 375 | — | — | 265–275 | 4.5 | Scarcely formed | Scarcely accumulated | Scarcely formed | 71 | 0 |
| Ex. 3 | BBP | 370 | PPG#400 | 10 | 265–275 | 5.0 | Scarcely formed | Scarcely accumulated | Scarcely formed | 85 | 0 |
| Ex. 4 | DBP | 340 | PPG#400 | 20 | 265–275 | 20.0 | Scarcely formed | Scarcely accumulated | Scarcely formed | 77 | <0.1 |
| Ex. 5 | TCP | 420 | PPG#400 | 21 | 265–275 | 0.7 | Scarcely formed | Scarcely accumulated | Scarcely formed | 55 | <0.1 |
| Ex. 6 | BBP | 370 | PEG#300 | 6 | 265–275 | 5.0 | Scarcely formed | Scarcely accumulated | Scarcely formed | 77 | <0.1 |
| Ex. 7 | BBP | 370 | Glycerol | 8 | 265–275 | 5.0 | Scarcely formed | Scarcely accumulated | Scarcely formed | 58 | <0.1 |
| Ex. 8 | BBP | 370 | TEG | 5 | 265–275 | 5.0 | Scarcely formed | Scarcely accumulated | Scarcely formed | 78 | <0.1 |
| Ex. 9 | BBP | 370 | Tri-decanol | 25 | 265–275 | 5.0 | Scarcely formed | Scarcely accumulated | Scarcely formed | 50 | <0.1 |
| Ex. 10 | BBP | 370 | PPG#400 | 5.5 | 265–275 | 5.0 | Scarcely formed | Scarcely accumulated | Scarcely formed | 44 | 0.4 |

(Note):
(*1) Kind of solvent:
DMEP = Di(2-methoxyethyl) phthalate
DEDB = Diethylene glycol dibenzoate
BBP = Benzylbutyl phthalate
DBP = Dibutyl phthalate
TCP = Tricresyl phosphate
(*2) Kind of solubilizing agent:
PPG = Polypropylene glycol
PEG = Polyethylene glycol
TEG = Tetraethylene glycol
(*3) Amount of solubilizing agent added: A charged amount (parts by weight) of the solubilizing agent per 100 parts by weight of the oligomer charged.
(*4) Residual rate of melt phase: The residual rate was determined by charging each of mixtures of the same charge compositions as in Examples and Comparative Examples in a graduated test tube, heating the mixture to the depolymerization temperature of the oligomer, reading a volume of a melt phase of the oligomer formed from the graduations and comparing the value with a volume of a melt phase of the oligomer formed where the solvent was changed to liquid paraffin (substantially having no dissolving power for the oligomer).

Comparative Example 1

A 300-ml flask, to which a receiver cooled with chilled water was connected, was charged with 40 g of the glycolic acid oligomer prepared in Synthesis Example 1, and 170 g of liquid paraffin (product of Kanto Chemical Co., Inc.) were added as an organic solvent. The mixture of the oligomer and solvent was heated to 265°–275° C. under reduced pressure of 90.0 kPa in a nitrogen gas atmosphere. It was visually confirmed that the oligomer formed a melt phase and underwent phase separation from the solvent. No dimeric cyclic ester was distilled out, and only the solvent was distilled out and collected in the receiver. Therefore, the heating was stopped in mid course. Almost all of the oligomer was formed into tar and remained as a residue. Depolymerization conditions and the interior state of the flask are shown collectively in Table 2.

Comparative Example 2

The operation was performed in the same manner as in Comparative Example 1 except that in Comparative Example 1, the organic solvent and the heating temperature were changed to o-dichlorobenzene (boiling point: about 180° C.; molecular weight: 147) and 170°–180° C., respectively. It was visually confirmed that the oligomer formed a melt phase and underwent phase separation from the solvent. Since the boiling point of the solvent was low, no dimeric cyclic ester was distilled out together with the solvent by the heating, and only the solvent was distilled out and collected in the receiver. Therefore, the heating was stopped in mid course. Depolymerization conditions and the interior state of the flask are shown collectively in Table 2.

Comparative Example 3

The operation was performed in the same manner as in Comparative Example 1 except that in Comparative Example 1, the organic solvent and the heating temperature were changed to 1,2,4-trichlorobenzene (boiling point: 213° C.; molecular weight: 181) and 200°–210° C., respectively. It was visually confirmed that the oligomer formed a melt phase and underwent phase separation from the solvent. Since the boiling point of the solvent was low, no dimeric cyclic ester was distilled out together with the solvent, and only the solvent was distilled out and collected in the receiver. Therefore, the heating was stopped in mid course. Depolymerization conditions and the interior state of the flask are shown collectively in Table 2.

Comparative Example 4

The operation was performed in the same manner as in Comparative Example 1 except that in Comparative Example 1, the organic solvent, the pressure inside the flask and the heating temperature were changed to benzylbutyl phthalate (boiling point: 370° C.; molecular weight: 312), 5.0 kPa and 265°–310° C., respectively. It was visually confirmed that the oligomer formed a melt phase and underwent phase separation from the solvent. A dimeric cyclic ester was scarcely observed being distilled out up to a flask temperature of about 290° C. When the flask temperature exceeded about 290° C., benzylbutyl phthalate started to be decomposed, and phthalic anhydride came to be distilled out. Since the oligomer was in a state of phase separation from the solvent, a dimeric cyclic ester was formed only in an extremely small amount. Depolymerization conditions and the interior state of the flask are shown collectively in Table 2.

Comparative Example 5

The operation was performed in the same manner as in Comparative Example 1 except that in Comparative Example 1, the organic solvent, the pressure inside the flask and the heating temperature were changed to dibutyl phthalate (boiling point: 340° C.; molecular weight: 278), 20.0 kPa and 265°–305° C., respectively. It was visually confirmed that the oligomer formed a melt phase and underwent phase separation from the solvent. A dimeric cyclic ester was scarcely observed being distilled out up to a flask temperature of about 290° C. When the flask temperature exceeded about 290° C., dibutyl phthalate started to be decomposed, and phthalic anhydride came to be distilled out. Since the oligomer was in a state of phase separation from the solvent, no dimeric cyclic ester was formed. Depolymerization conditions and the interior state of the flask are shown collectively in Table 2.

Comparative Example 6

The operation was performed in the same manner as in Comparative Example 1 except that in Comparative Example 1, the organic solvent, the pressure inside the flask and the heating temperature were changed to tricresyl phosphate (boiling point: about 420° C.; molecular weight: 368), 1.0 kPa and 265°–310° C., respectively. It was visually confirmed that the oligomer formed a melt phase and underwent phase separation from the solvent. A dimeric cyclic ester was scarcely observed being distilled out up to a flask temperature of about 300° C. When the flask temperature exceeded about 300° C., tricresyl phthalate started to be decomposed, and the liquid in the flask turned deep-black. Since the oligomer was in a state of phase separation from the solvent, no dimeric cyclic ester was formed. Depolymerization conditions and the interior state of the flask are shown collectively in Table 2.

Comparative Example 7

The operation was performed in the same manner as in Comparative Example 1 except that in Comparative Example 1, the organic solvent was changed to benzylbutyl phthalate (boiling point: 370° C.; molecular weight: 312), 0.8 g of polypropylene glycol (PPG#400, product of Junsei Chemical Co., Ltd.; boiling point: at least about 450° C.; molecular weight: about 400) was added as a solubilizing agent, the pressure inside the flask was changed to 5.0 kPa, and the mixture was heated up to 265°–275° C. It was visually confirmed that since the amount of the solubilizing agent was small, a considerable amount of the oligomer formed a melt phase and underwent phase separation from the solvent. Since the oligomer was in a state of phase separation from the solvent, a slight amount of a dimeric cyclic ester was observed being distilled out early, but the distilling-out stopped before long. Depolymerization conditions and the interior state of the flask are shown collectively in Table 2.

Comparative Example 8

The operation was performed in the same manner as in Comparative Example 1 except that in Comparative Example 1, the organic solvent was changed to benzylbutyl phthalate (boiling point: 370° C.; molecular weight: 312), 0.8 g of polyethylene glycol (PEG#300, product of Junsei Chemical Co., Ltd.; boiling point: at least about 400° C.; molecular weight: about 300) was added as a solubilizing agent, the pressure inside the flask was changed to 5.0 kPa, and the mixture was heated up to 265°–275° C. It was visually confirmed that since the amount of the solubilizing agent was small, a considerable amount of the oligomer formed a melt phase and underwent phase separation from the solvent. Since the oligomer was in a state of phase separation from the solvent, a slight amount of a dimeric cyclic ester was observed being distilled out early, but the distilling-out stopped before long. Depolymerization conditions and the interior state of the flask are shown collectively in Table 2.

TABLE 2

| | Depolymerization conditions | | | | | | Interior State of flask | | | Residual | |
| --- | --- | --- | --- | --- | --- | --- | --- | --- | --- | --- | --- |
| | Solvent | | Solubilizing agent | | Inside temp. | Inside pressure | Melt | Accumulation of DCE on | | Yield of | rate of melt phase |
| | Kind (*1) | BP (°C.) | Kind (*2) | Amount added (parts) (*3) | of flask (°C.) | of flask (kPa) | phase of oligomer | inner wall of line | Tar formation | DCE (wt. %) | (v/v) (*4) |
| Comp. Ex. 1 | Liq. paraffin | — | — | — | 265–275 | 90.0 | Almost all | — | Great | 0 | 1 |
| Comp. Ex. 2 | o-DCB | 180 | — | — | 170–180 | 90.0 | Almost all | — | Great | 0 | 1 |
| Comp. Ex. 3 | 1,2,4-TCB | 213 | — | — | 200–210 | 90.0 | Almost all | — | Great | 0 | 1 |
| Comp. Ex. 4 | BBP | 370 | — | — | 265–310 | 5.0 | Great | Scarcely accumulated | Great | 3 | 0.7 |
| Comp. Ex. 5 | DBP | 340 | — | — | 265–305 | 20.0 | Almost all | — | Great | 0 | 1 |
| Comp. | TCP | 420 | — | — | 265–310 | 1.0 | Almost all | — | Great | 0 | 1 |

TABLE 2-continued

| | Depolymerization conditions | | | | | | Interior State of flask | | Yield of DCE (wt. %) | Residual rate of melt phase (v/v) (*4) |
|---|---|---|---|---|---|---|---|---|---|---|
| | Solvent | | Solubilizing agent | | Inside temp. of flask (°C.) | Inside pressure of flask (kPa) | Melt phase of oligomer | Accumulation of DCE on inner wall of line | Tar formation | | |
| | Kind (*1) | BP (°C.) | Kind (*2) | Amount added (parts) (*3) | | | | | | | |
| Ex. 6 Comp. Ex. 7 | BBP | 370 | PPG#400 | 2 | 265–275 | 5.0 | Great | Scarcely accumulated | Great | 6 | 0.6 |
| Comp. Ex. 8 | BBP | 370 | PEG#300 | 2 | 265–275 | 5.0 | Great | Scarcely accumulated | Great | 5 | 0.6 |

(Note):
(*1) Kind of solvent:
o-DCB = o-Dichlorobenzene
1,2,4-TCB = 1,2,4-Trichlorobenzene
DBP = Dibutyl phthalate
BBP = Benzylbutyl phthalate
TCP = Tricresyl phosphate
(*2) Kind of solubilizing agent:
PPG = Polypropylene glycol
PEG = Polyethylene glycol
(*3) Amount of solubilizing agent added:
A charged amount (parts by weight) of the solubilizing agent per 100 parts by weight of the oligomer charged.
(*4) Residual rate of melt phase:
Determined in the same manner as in Note (*4) to Table 1.

EXAMPLE 11

A 10-liter flask, to which a receiver cooled with chilled water was connected, was charged with 1 kg of the glycolic acid oligomer prepared in Synthesis Example 1, 4 kg of benzylbutyl phthalate (boiling point: 370° C.; molecular weight: 312) and 150 g of polypropylene glycol (PPG#400, product of Junsei Chemical Co., Ltd.; boiling point: at least about 450° C.; molecular weight: about 400). The mixture was heated to 265°–275° C. under reduced pressure of 5.0 kPa in a nitrogen gas atmosphere. The oligomer was observed dissolving uniformly in the solvent without undergoing phase separation. The heating was continued at a temperature within the above range to depolymerize the oligomer, and a dimeric cyclic ester formed was distilled out together with the solvent. Cyclohexane about twice as much as the distillate by volume was added as a non-solvent to the distillate collected in the receiver. The resultant mixture was left at rest overnight to deposit a crystal of the dimeric cyclic ester. The crystal deposited was collected by filtration, washed with cyclohexane, recrystallized from ethyl acetate and then dried under reduced pressure. As a result, 0.75 kg of the dimeric cyclic ester was collected. This experiment revealed that according to the preparation process of the present invention, a scale can be enlarged.

EXAMPLE 12

A crude dimeric cyclic ester was prepared by using the glycolic acid oligomer prepared in Synthesis Example 1 and depolymerizing the oligomer at 270°–320° C. under reduced pressure of 0.1–1.0 kPa in a nitrogen gas atmosphere in accordance with the conventional depolymerization process making use of a sublimation tube. The purity of the crude dimeric cyclic ester was 89.8% (as measured by gas chromatography). A 300-ml flask, to which a receiver cooled with chilled water was connected, was charged with 20 g of the crude dimeric cyclic ester and 200 g of benzylbutyl phthalate (boiling point: 370° C.; molecular weight: 312) as a solvent for co-distilling out the dimeric cyclic ester to distill out the dimeric cyclic ester together with the solvent at 265°–275° C. under reduced pressure of 5.0 kPa in a nitrogen gas atmosphere. Cyclohexane about twice as much as the distillate by volume was added as a non-solvent to the distillate collected in the receiver. The resultant mixture was left at rest overnight to deposit a crystal of the dimeric cyclic ester. The crystal deposited was collected by filtration, washed with cyclohexane, recrystallized from ethyl acetate and then dried under reduced pressure. The purity of the dimeric cyclic ester thus obtained was 99.9%.

The purity was measured by gas chromatography under the following conditions:

(1) Sample solution: 0.1 wt. % acetonitrile solution
(2) Amount of sample: 1 μl
(3) Column: TC-17 (capillary column, product of GL Sciences Inc.)
 Inner diameter: 0.53 mm, length: 30 m
 Packing: phenylpolysiloxane/methylpolysiloxane mixture
 Packing: Film layer 1.0 μm
(4) Temperature: 80° C. (retention: 5 minutes), raised to 290° C. at a rate of 5° C./min.
 Detecting part: 300° C.
(5) Carrier gas: helium, 30 ml/min.

We claim:

1. A process for preparing a dimeric cyclic ester of an α-hydroxycarboxylic acid by depolymerizing a corresponding α-hydroxycarboxylic acid oligomer, which comprises the steps of:

(1) heating a mixture containing the α-hydroxycarboxylic acid oligomer and at least one high-boiling polar organic solvent having a boiling point within a range of 230°–450° C. to a temperature, at which the depolymerization of the oligomer takes place, under atmospheric pressure or reduced pressure;

(2) dissolving the oligomer in the solvent until a residual rate of a melt phase of the oligomer reaches 0.5 or lower;

(3) further continuing the heating at the temperature, at which the depolymerization of the oligomer takes place, to depolymerize the oligomer;

(4) distilling out the dimeric cyclic ester formed together with the high-boiling polar organic solvent; and (5) recovering the dimeric cyclic ester from the distillate.

2. The process according to claim 1, wherein the high-boiling polar organic solvent is a non-basic polar organic solvent having a molecular weight within a range of 150–500.

3. The process according to claim 1, wherein the high-boiling polar organic solvent is at least one selected from the group consisting of alkoxyalkyl esters of aromatic carboxylic acids, alkoxyalkyl esters of aliphatic carboxylic acids, polyalkylene glycol ethers, polyalkylene glycol esters, aromatic carboxylic esters, aliphatic carboxylic esters, aromatic ethers, aliphatic ethers, aromatic phosphoric esters, aliphatic phosphoric esters, aliphatic imide compounds, aliphatic amide compounds and polyhalogenated aromatic hydrocarbons.

4. The process according to claim 1, wherein the high-boiling polar organic solvent is at least one selected from the group consisting of bis(alkoxyalkyl) phthalates, dialkylene glycol dibenzoates and polyethylene glycol ethers.

5. The process according to claim 1, wherein the high-boiling polar organic solvent is di(2-methoxyethyl) phthalate, diethylene glycol dibenzoate, benzylbutyl phthalate, dibutyl phthalate or tricresyl phosphate.

6. The process according to claim 1, wherein the mixture containing the α-hydroxycarboxylic acid oligomer and at least one high-boiling polar organic solvent further comprises a solubilizing agent having an effect of enhancing the solubility of the a-hydroxycarboxylic acid oligomer in the high-boiling polar organic solvent.

7. The process according to claim 6, wherein the solubilizing agent is a non-basic compound which is compatible with or soluble in the high-boiling polar organic solvent and has a boiling point of at least 230° C. and a hydrophilic functional group.

8. The process according to claim 6, wherein the solubilizing agent is at least one non-basic organic compound having a boiling point of at least 230° C. and selected from the group consisting of monohydric and polyhydric alcohols, phenols, aliphatic monocarboxylic and polycarboxylic acids, aliphatic amides, aliphatic imides and sulfones.

9. The process according to claim 6, wherein the solubilizing agent is a monohydric or polyhydric alcohol.

10. The process according to claim 9, wherein the monohydric or polyhydric alcohol is polypropylene glycol, polyethylene glycol, glycerol or tridecanol.

11. The process according to claim 6, wherein the high-boiling polar organic solvent is at least one selected from the group consisting of aromatic carboxylic esters, aliphatic carboxylic esters, aromatic ethers, aliphatic ethers, aromatic phosphoric esters, aliphatic phosphoric esters, aliphatic imide compounds, aliphatic amide compounds and polyhalogenated aromatic hydrocarbons.

12. The process according to claim 6, wherein the high-boiling polar organic solvent is benzylbutyl phthalate, dibutyl phthalate or tricresyl phosphate, and the solubilizing agent is polypropylene glycol, polyethylene glycol, glycerol or tridecanol.

13. The process according to claim 1, wherein the α-hydroxycarboxylic acid oligomer is an oligomer of glycolic acid, lactic acid, α-hydroxybutyric acid or α-hydroxyvaleric acid.

14. The process according to claim 1, wherein the a α-hydroxycarboxylic acid oligomer has a melting point Tm of at least 140° C., which is detected at the time the oligomer is heated at a rate of 10° C./min in an inert atmosphere by means of a differential scanning calorimeter (DSC).

15. The process according to claim 1, wherein the dimeric cyclic ester of the α-hydroxycarboxylic acid is glycolide or lactide.

16. The process according to claim 1, wherein the α-hydroxycarboxylic acid oligomer is a glycolic acid oligomer, and the dimeric cyclic ester of the α-hydroxycarboxylic acid is glycolide.

17. The process according to claim 1, wherein the depolymerization of the α-hydroxycarboxylic acid oligomer is performed by heating the mixture containing the α-hydroxycarboxylic acid oligomer and at least one high-boiling polar organic solvent to a temperature of at least 230° C.

18. The process according to claim 1, wherein the mixture containing the high-boiling polar organic solvent in a proportion of 30–5,000 parts by weight per 100 parts by weight of the α-hydroxycarboxylic acid oligomer is heated to a temperature of 230°–320° C. under atmospheric pressure or reduced pressure.

19. The process according to claim 6, wherein the mixture containing the high-boiling polar organic solvent and the solubilizing agent in proportions of 30–5,000 parts by weight and 0.1–500 parts by weight, respectively, per 100 parts by weight of the α-hydroxycarboxylic acid oligomer is heated to a temperature of 230°–320° C. under atmospheric pressure or reduced pressure.

20. The process according to claim 1, wherein the recovery of the dimeric cyclic ester from the distillate is carried out by cooling the distillate and optionally adding a non-solvent for the dimeric cyclic ester to solidify and deposit the dimeric cyclic ester, and separating and recovering the deposited dimeric cyclic ester.

21. A process for purifying a crude dimeric cyclic ester of an α-hydroxycarboxylic acid, which comprises the steps of:

heating a mixture containing the crude dimeric cyclic ester of the α-hydroxycarboxylic acid and at least one high-boiling polar organic solvent having a boiling point within a range of 230°–450° C. to a temperature of at least 230° C. under atmospheric pressure or reduced pressure to form a uniform solution free from phase separation between the individual components;

further continuing the heating in the state of uniform solution phase to distill out the dimeric cyclic ester together with the high-boiling polar organic solvent; and recovering the dimeric cyclic ester from the distillate.

* * * * *

UNITED STATES PATENT AND TRADEMARK OFFICE
CERTIFICATE OF CORRECTION

PATENT NO. : 5,830,991
DATED : November 3, 1998
INVENTOR(S) : Zenya Shiiki et al It is certified that error appears in the above-identified patent and that said Letters Patent is hereby corrected as shown below:

Claim 14, column 20, line 5, delete "a".

Signed and Sealed this

Twenty-third Day of March, 1999

Attest:

Q. TODD DICKINSON

*Attesting Officer*       *Acting Commissioner of Patents and Trademarks*